United States Patent
Roser et al.

(10) Patent No.: US 6,221,575 B1
(45) Date of Patent: *Apr. 24, 2001

(54) METHODS FOR PRODUCING DRIED STORAGE-STABLE PLATELETS AND COMPOSITIONS OBTAINED THEREBY

(75) Inventors: Bruce J. Roser, Cambridge; Valentine Menys, Cherry Hinton; Lynda Grandage, Haslingfield, all of (GB); Diana Phipps, Nassington (NL)

(73) Assignee: Quadrant Holdings Cambridge Ltd., Nottingham (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/019,935

(22) Filed: Feb. 6, 1998

Related U.S. Application Data

(60) Provisional application No. 60/037,493, filed on Feb. 7, 1997.

(51) Int. Cl.$^7$ .................................................. C12N 5/00
(52) U.S. Cl. ........................... 435/2; 435/374; 436/18; 424/532; 536/123.13
(58) Field of Search ........................ 435/2, 374; 436/18; 424/532; 536/123.13

(56) References Cited

U.S. PATENT DOCUMENTS

| | | |
|---|---|---|
| 4,251,995 | 2/1981 | Pert et al. . |
| 4,891,319 | 1/1990 | Roser . |
| 5,026,566 | 6/1991 | Roser . |
| 5,149,653 | 9/1992 | Roser . |
| 5,242,792 | 9/1993 | Rudolph et al. . |
| 5,332,578 | 7/1994 | Chao . |
| 5,428,008 | 6/1995 | Chao et al. . |
| 5,827,741 * | 10/1998 | Beattie et al. ....................... 435/374 |
| 5,902,608 * | 5/1999 | Read et al. .......................... 424/532 |
| 5,958,670 * | 9/1999 | Goodrich, Jr. et al. ................. 435/2 |

FOREIGN PATENT DOCUMENTS

| | | |
|---|---|---|
| 0 141 939 A2 | 5/1985 | (EP) . |
| 0 508 496 | 10/1992 | (EP) . |
| 0 356 257 B1 | 3/1995 | (EP) . |
| 0 668 013 | 8/1995 | (EP) . |
| 6154318 | 6/1994 | (JP) . |
| 920687 | 1/1997 | (JP) . |
| WO 86/03938 | 7/1986 | (WO) . |
| WO 87/05300 | 9/1987 | (WO) . |
| WO 90/04329 | 5/1990 | (WO) . |
| WO 93/00806 | 1/1993 | (WO) . |
| WO 93/14191 | 7/1993 | (WO) . |

OTHER PUBLICATIONS

Ali et al., "Platelet concentrates stored for 5 days in a reduced volume of plasma mainatian hemostatic function and viability" *Transfusion* 34:44–47 (1994).

Argall, M.E. and Smith, G.D., "The use of trehalose–stabilized lyophilized methanol dehydrogenase from *Hyphomicrobium* X for the detection of methanol" *Biochem. Mol. Biol. Int.* 30:491–497 (1993).

Bateson et al., "Electrokinetic properties of human cryopreserved platelets" *Transfusion Med.* 4:213–219 (1994).

Blajchman et al., "The contribution of the haematocrit to thrombocytopenic bleeding in experimental animals" *Brit. J. Haematol.* 86:347–350 (1994).

Blakeley et al., "Dry instant blood typing plate for bedside use" *The Lancet* 336:854–855 (1990).

Böck et al., "Cryopreservation of human platelets with dimethyl sulfoxide: Changes in biochemistry and cell function" *Transfusion* 35:921–924 (1995).

Chao et al., "Infusible platelet membrane microvesicles: A potential transfusion subsitute for platelets" *Transfusion* 36:536–542 (1996).

Colaço et al., "Extraordinary stability of enzymes dried in trehalose: Simplified molecular biology" *Bio/Tech.* 10:1006–1011 (1992).

Colaço et al., "Trehalose stabilisation of biological molecules" *Biotechnol. Intl.*, pp. 345–350 (1992).

Colvin et al., "Effect of dry–heating of coagulation factor concentrates at 80° for 72 hours on transmission of non–A, non–B hepatitis" *The Lancet*, pp 814–816 (Oct. 8, 1988).

Crook, M. and Crawford, N., "Platelet surface charge heterogeneity: Characterization of human platelet subpopulations separated by high voltage continuous flow electrophoresis" *Br. J. Haematol.* 69:265–273 (1988).

Crowe et al., "Preservation of structural and functional activity in lyophilized sarcoplasmic reticulum" *Arch. Biochem. Biophys.* 220(2):477–484 (1983).

Crowe et al., "Effects of carbohydrates on membrane stability at low water activities" *Biochim. Biophys. Acta* 769:141–150 (1984).

Dale, G.L., "High–efficiency entrapment of enzymes in resealed red cell ghosts by dialysis" *Meth. Enzymol.* 149:229–234 (1987).

Eleutherio et al., "Role of the trehalose carrier in dehydration resistance of *Saccharomyces cerevisiae*" *Biochim Biophys Acta* 1156:263–266 (1993).

Holme et al., "Evaluation of platelet concentrates stored for 5 days with reduced plasma volume" *Transfusion* 34:39–43 (1994).

(List continued on next page.)

Primary Examiner—Leon B. Lankford, Jr.
(74) *Attorney, Agent, or Firm*—Morrison & Foerster LLP

(57) ABSTRACT

The invention provides methods for drying platelets to obtain compositions which are storage stable over a wide range of temperatures and for an extended period of time. The invention also provides compositions obtained thereby and devices for use therein.

11 Claims, 5 Drawing Sheets

OTHER PUBLICATIONS

Hottiger et al., "The role of trehalose synthesis for the acquisition of thermotolerance in yeast" *Eur. J. Biochem.* 219:187–193 (1994).

Hughes, K. and Crawford, N., "Reversible electropermeabilisation of human and rat blood platelets: Evaluation of morphological and functional integrity 'in vitro' and 'in vivo'" *Biochem. Biophys. Acta 981*:277–287 (1989).

Hughes, K. and Crawford, N., "Reversibly electropermeabilized platelets: Potential use as vehicles for drug delivery" *634th Meeting, Bath, Biochemical Society Trans.* 18(5):871–873 (1990).

Ihler, G.M. and Tsang, H., "Hypotonic hemolysis methods for entrapment of agents in resealed erythrocytes" *Meth. Enzymol. 149*:221–229 (1987).

Magnani et al., "Targeting antiretroviral nucleoside analogues in phosphorylated form to macrophages: In vitro and in vivo studies" *Proc. Natl. Acad Sci. USA 89*:6477–6481 (1992).

Moroff et al., "Effect on platelet properties of exposure to temperatures below 20° C for short periods during storage at 20 to 24° C" *Transfusion 34*:317–321 (1994).

Okada, C.Y. and Rechsteiner, M., "Introduction of macromolecules into cultured mammalian cells by osmotic lysis of pinocytic vesicles" *Cell 29*:33–41 (1982).

Read et al., "Preservation of hemostatic and structural properties of rehydrated lyophilized platelets: Potential for long–term storage of dried platelets for transfusion" *Proc. Natl. Acad. Sci. USA 92*:397–401 (1995).

Rechsteiner, M., "Osmotic lysis of pinosomes" *Meth. Enzymol. 149*:42–48 (1987).

Roser, B., "Approach to premium dried foods" *Trends in Food Sci. and Tech.*, pp. 166–169 (Jul. 1991).

Roser, B., "Trehalose drying: A novel replacement for freeze–drying" *BioPharm. 4*:47–53 (1991).

Roser, B. and Colaço, C., "A sweeter way to fresher food" *New Scientist*, pp. 25–28. (May 1993).

Tablin et al., "Membrane phase transition of intact human platelets: Correlation with cold–induced activation" *J. Cell. Physiol. 168*:305–313 (1996).

\* cited by examiner

METHODS FOR PRODUCING DRIED STORAGE-STABLE PLATELETS AND COMPOSITIONS OBTAINED THEREBY

CROSS-REFERENCE TO RELATED APPLICATIONS

This application claims priority to and is a continuation in-part of U.S. patent application Ser. No. 60/037,493 filed Feb. 7, 1997 which is incorporated by reference herein in its entirety.

STATEMENT OF RIGHTS TO INVENTIONS MADE UNDER FEDERALLY SPONSORED RESEARCH

Not applicable.

TECHNICAL FIELD

This invention relates to methods of preserving platelets. Methods of use thereof and compositions obtained thereby are also provided. Bags for preserving, storing and resuspending the platelets are also provided.

BACKGROUND ART

Blood platelets are one of the complex components involved in maintaining hemostasis. When a blood vessel wall is damaged, platelets adhere to exposed surfaces composed of collagen, microfibrils, and basement membrane. Adherent platelets promote the recruitment of other platelets to form an aggregated mass called a hemostatic platelet plug. The result is to activate coagulation proteins which provide the network to stabilize the platelet plug and reduce bleeding, allowing tissue repairs to occur.

Platelets are transfused to patients for many clinical indications. For instance, platelet infusions are used to correct deficiencies or dysfunctions of circulating platelets as a result of trauma, disease, or drug induced dysfunction. Patients suffering from idiopathic thrombocytopenia and those undergoing ablative chemotherapy are treated with platelet infusions. The increasing use of ablative chemotherapy for a wide variety of malignancies has resulted in an increased need for replacement platelet therapy.

A major difficulty in using isolated platelets is their short shelf-life. Platelets are only approved by the Food and Drug Administration (FDA) for storage in a liquid state for up to five days at room temperature, during which time the functional properties rapidly deteriorate. This causes many logistic problems in both civilian and military medicine.

Further drawbacks of storing platelets in a liquid state include the necessity of considerable storage space and constant agitation within bags of specially developed gas permeable plastics. Typically, platelets are stored in a suspending plasma volume of 45 to 65 mL. Recently, a study reported liquid storage establishing a minimum plasma volume of 30–50 mL. Home et al. (1994) Transfusion 34:39; and Ali et al. (1994) Transfusion 34:44. This storage method still requires considerable space, however, and the shelf life is not extended beyond approximately five days. The major problem with liquid storage is that the platelets need to be stored above 20° C. as even short periods of exposure to lower temperatures during storage result in substantial changes in their in vivo and in vitro properties. Moroff et al. (1994) Transfusion 34:317. As this storage usually also requires agitation of the platelets during storage at about 20–24°°C., often in the presence of glucose, this presents optimal conditions for bacterial growth which is a major problem with the storage of liquid platelets.

To minimize the problems of bacterial growth, refrigerated storage at 4° C. or frozen storage at –80° C. has been proposed. However, this requires methods to prevent the cold-activation of the stored platelets. The use of anti-freeze glycoproteins have also been suggested for use in preservation of platelets. Tablin et al. (1996) in Frozen Platelets and Platelet Substitutes in Transfusion Medicine, Uniformed Services University of the Health Sciences (the "Bethesda meeting"). This method would however, require extensive washing of the platelets, to remove the anti-freeze proteins, before therapeutic use. This drawback is also seen with the methods of freezing platelets involving the use of DMSO which would again require extensive washing of the platelets before therapeutic use. Bock et al. (1995) Transfusion 53:921. A method of storing platelets by freeze drying has been described. Bateson et al. (1994) Transfusion Med. 4:213, EPA 0356257. Platelets are activated during the process of freeze drying and can only be used as a hematology standard and the electrokinetic properties of the preserved platelets are different from those of fresh matched platelets. Oliver et al. the Bethesda Meeting. Other attempts at lyophilizing platelets have met with suboptimal results. Bode (1993a and b) First and Second Triannual Reports, (respectively) Evaluation of Dried Storage of Platelets for Transfusion: Physiologic Integrity and Hemostatic Functionality. DNR Grant No. N00014-92-J-1244. Fixing the platelets prior to freeze-drying improves their function but these freeze-dried platelets need to be stored frozen at –80° C. Read et al. (1995) Proc. Natl. Acad. Sci. 92:397.

At the Bethesda meeting, the following ideal attributes for platelets were stated: prevention of bleeding for up to 24 hours; 20% of infused platelets in circulation after 24 hours; long-term storage outside of freezers or refrigerators; lightweight, durable and easy to transport; easy to use without the need of centrifugation; non-immunogenic; sterile; and donor check possible after three months. The meeting also highlighted the lack of in vivo models for the evaluation of, and data on the in vivo evaluation of, most human platelet preparations being developed. One exception was the reticulo-endothelial-system-block thrombocytopenic rabbit model of Blajchman (RES-block model) which enabled the evaluation of human platelet efficacy in an animal model. Ali et al. (1994) Transfusion 34:44; and Blajchman et al. (1994) Brit. J. Haematol. 86:347.

Platelet products have also been proposed for use as platelet substitutes and as independently therapeutic agents. These products also offer a longer shelf life than intact platelets. Platelet membrane vesicles have been prepared by a number of methods and have been shown to reduce bleeding time in a rabbit model. Chao et al. (1996) Transfusion 36:536–542; and U.S. Pat. Nos. 5,428,008 and 5,332, 578. Dried, powdered platelet membranes have also been prepared as an immunoadsorbent. EP 141939.

It would be useful to fulfill many of the goals enumerated above. It would be especially useful to have a method for storing platelets at ambient temperatures for periods of time greater than five days. These criteria immediately eliminate the applicability of all current liquid and cryopreserved platelet preparations. Even more advantageous would be a method for long term storage of dried platelets, particularly with regard to the problem of bacterial growth during liquid storage. Storage of dried platelets would require less space than storage of platelets in liquid or as a frozen solid due to reduced volume and would not require constant agitation in the liquid state, thus enabling considerable savings on storage and transport costs. This would also enable the use of platelets in areas of the world that do not otherwise have adequate storage or transport facilities. Banking of HLA-matched dried platelets would also find use in treatment of alloimmunized patients.

Trehalose, ω-D-glucopyranosyl-ω-D-glucopyranoside, is a naturally occurring, non-reducing disaccharide which was initially found to be associated with the prevention of desiccation damage in certain plants and animals which can dry out without damage and revive when rehydrated. Trehalose has been shown to be useful in preventing denaturation of proteins, viruses and foodstuffs during desiccation and subsequent storage. See U.S. Pat. Nos. 4,891,319; 5,149,653; 5,026,566; Blakeley et al. (1990) *Lancet* 336:854; Roser (July 1991) *Trends in Food Sci. and Tech.*, pp. 166–169; Colaco et al. (1992) *Biotechnol. Internat.*, pp. 345–350; Roser (1991) *BioPharm.* 4:47; Colaco et al. (1992) *Bio/Tech.* 10:1007; and Roser et al. (May 1993) *New Scientist*, pp. 25–28.

In nature, trehalose stabilizes the cell membrane under various stressful conditions. Trehalose is linked to the ability of yeast cells to survive complete dehydration. Eleutherio et al. (1993) *Biochim Biophys Acta* 1156:263. Trehalose is also known to stabilize lyophilized proteins, such as methanol dehydrogenase (Argall and Smith (1993) *Biochem. Mol. Biol. Int.* 30:491), and to confer thermoprotection to enzymes from yeast. Hottiger et al. (1994) *Eur. J. Biochem.* 219:187.

Trehalose has been used to stabilize lyophilized sarcoplasmic reticulum and liposomes. Crowe, J. et al. (1983) *Arch. Biochem. Biophys.* 220:470–484; and Crowe, L. et al. (1984) *Biochim. Biophys. Acta* 769:141–150. In both these instances, trehalose was added to the solution in which the membranes or liposomes were suspended, the mixture was frozen and freeze dried. Trehalose was found to prevent membrane phase transition. Trehalose has been suggested for use in the cryopreservation of platelets; the loading of these platelets by freeze-induced membrane phase transition has been reported to prevent cold-induced activation during freezing. Oliver et al. the Bethesda Meeting. However, these platelets need to be stored frozen at −80° C. and the use of DMSO for the cryopreservation would require the platelets to be washed extensively before therapeutic use Oliver et al. and Crowe, L. et al. (1996) the Bethesda Meeting. Although a number of carbohydrates have been suggested for use in lyophilizing red blood cells, both trehalose and sucrose were found to be unsuitable. EP 356,257.

The methods described herein provide methods for preserving platelets by drying and the compositions obtained thereby. The dried platelets can be stored indefinitely at ambient temperatures. During storage the functional properties of the platelets are unchanged.

All references cited herein, both supra and infra, are hereby incorporated herein by reference.

SUMMARY OF THE INVENTION

The present invention provides methods of stabilizing platelets. The methods of stabilizing platelets for storage include loading platelets with an effective amount of trehalose, and drying the treated platelets in the presence of an effective amount of trehalose. The invention also includes compositions comprising the dried platelets ("QuadroCytes™") and platelets reconstituted from the dried preparations.

In another aspect of the invention, compositions of platelets dried according to the invention are provided. The platelets are storage stable for an indefinite period of time and for at least six weeks at temperatures of ambient or above and, upon reconstitution, are suitable for use in any indication for which fresh platelets are used.

In another aspect of the invention, reconstituted, dried platelets are provided. The reconstituted platelets are suitable for use in any indication for which fresh platelets are used. Suitable indications for reconstituted dried platelets include, but are not limited to, transfusion.

In another aspect of the invention, a method is provided for delivering therapeutic agents. Suitable therapeutic agents include, but are not limited to, bioactive agents with hemostatic, wound healing and antiscarring activities. In another aspect of the invention, a method is provided for delivering these agents to the sites of haemostatic activity or to the reticulo-endothelial system.

In another aspect of the invention, a method is provided for producing platelets suitable for purification of platelet factors. This method includes treating platelets as described above, and drying and recovering the platelets. The recovered platelets are then used in purification of platelet factors.

In another aspect of the invention, sterile bags are provided for packaging the QuadroCytes™. The bags are suitable for aseptic drying and storage of the QuadroCytes™ and are particularly suitable for sterile rehydration of the QuadroCytes™. This method also allows for immediate infusion of the reconstituted platelets without the need to transfer to them another container, thus minimizing the risk of contamination. For instance, standard blood transfusion packs containing the dried platelets provide a sterile source of platelets by injection of rehydration media through the self-resealing inlet tube and the platelets can then be directly infused from the bags.

BEST MODE FOR CARRYING OUT THE INVENTION

Figure 1:
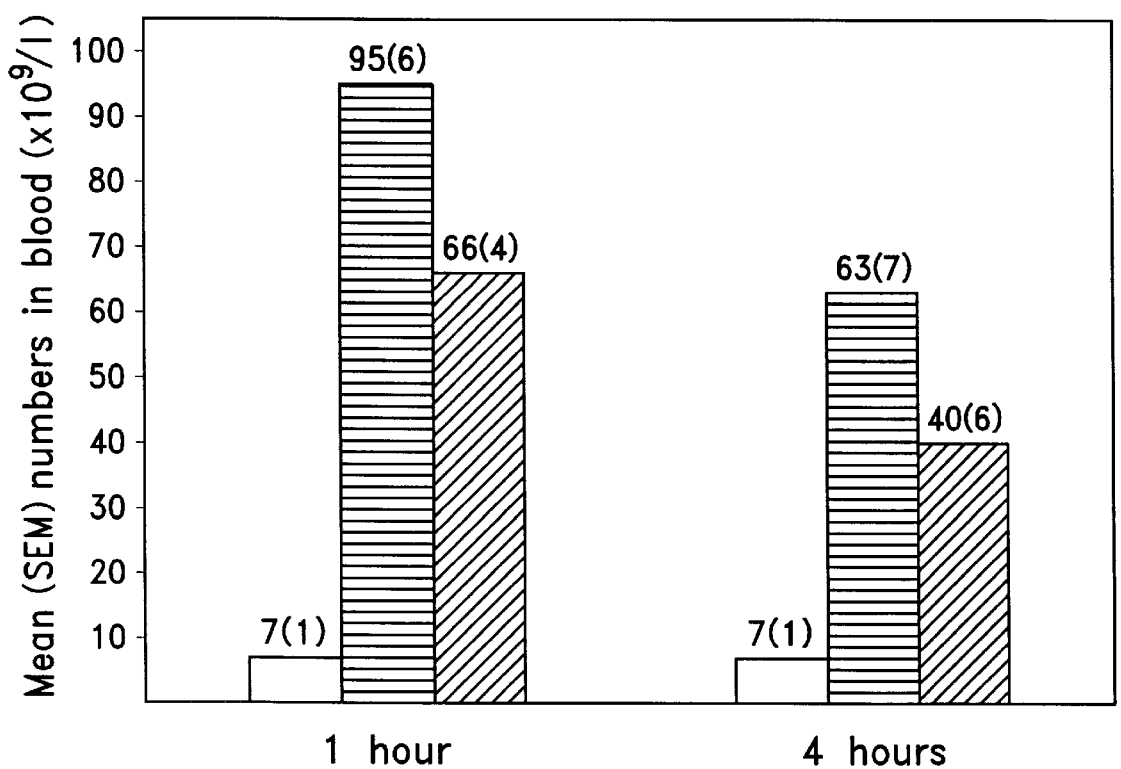
FIG. 1 is a bar graph depicting the blood numbers of platelets 1 and 4 hours after intravenous bolus injection of vehicle (open bar); platelets (horizontal-hatch bar) or rehydrated QuadroCytes™ (oblique-hatch bar).

The invention encompasses methods for preserving platelets. The methods include treating isolated platelets under conditions effective to introduce into the platelets an amount of internal trehalose effective to preserve the platelets during subsequent manipulations and drying the platelets in the presence of an amount of external trehalose effective to preserve the platelets on drying. The compositions thus obtained are termed QuadroCytes™.

The methods involve obtaining a suspension of platelets by any method known in the art. Typically, platelets are obtained by collecting blood into a suitable anticoagulant followed by obtaining platelet rich plasma (PRP) by any method known in the art. After a platelet pellet is obtained from the PRP by centrifugation, the platelet pellet is resuspended in a physiologically acceptable solution in an amount and under conditions effective to cause uptake or "introduction" of the trehalose into the platelets.

The trehalose is introduced into the platelets by any method known in the art. Suitable methods include, but are not limited to, electropermeabilisation, phase transition of the membrane, osmotic methods such as the use of organic osmolytes and pinocytosis, transient lysis methods such as acid shock and reversible cross-linking and the use of membrane permeable, esterase-labile trehalose derivatives. Effective means of electropermeabilisation are described for instance in the Examples herein and in Hughes and Crawford (1989), *Biochemica Biophysica Acta* 981:277–287; and Hughes and Crawford (1990) 634th Meeting, Bath, Biochemical Society Transactions 871–873. Effective means of phase transition of the membrane for platelet loading with trehalose are described for instance in Oliver et al. The Bethesda Meeting. Effective means of pinocytosis are described for instance in Okada and Rechsteiner (1982) *Cell* 29: 33; and Rechsteiner (1987) *Methods in Enzymology* 149: 42. Effective means of transient lysis are described for instance in Magnani et al. (1992) *Proc. Natl. Acad Sci.* 89:6477; Ihler and Tsang 1987 *Methods in Enzymology* 149: 221; and Dale (1987) *Methods in Enzymology* 149:229.

Preferably, the internal trehalose concentration is from about 10–125 mM. More preferably, the internal trehalose concentration is from about 30–100 mM. Even more preferably, the internal trehalose concentration is from about 50–75 mM.

The platelets are then resuspended in a drying buffer containing a stabilizing agent. The platelets can be concentrated prior to resuspension in the drying buffer. Any suitable method may be used to concentrate the platelets, including, but not limited to, differential centrifugation. Preferably, the treated platelets are centrifuged to form a pellet and the pellet is resuspended in the drying buffer containing a stabilizing agent. The stabilizing agent can be any carbohydrate that effects stabilization of the dried platelets. Preferably, the stabilizing agent is trehalose. Other suitable stabilizing agents include, but are not limited to, polyhydroxy agents that raise the glass transition temperature of dried formulations, such as serum albumin, haemocell, caesin hydrolysates, polyvinyl-pyrrolidone (PVP) and hydroxy ethyl starch (HES). Preferably, the stabilizing agent is a non-reducing carbohydrate. More preferably, the stabilizing agent is trehalose or derivatives thereof. Preferably, the resuspension/drying buffer is a buffered saline containing at least 1% trehalose and 1% serum albumin (SA).

Preferably, in the drying buffer, the trehalose concentration is about 1 to 30% and the SA concentration is about 0.5% to 5%. More preferably, the trehalose concentration is about 1 to 10% and the SA concentration is about 1 to 2.5%. This "external" concentration of stabilizing agent is any that provides effective preservation after drying. During resuspension, the external stabilizing agent concentration should be greater than the internal trehalose concentration so as to avoid platelet lysis. The effective combination of internal concentration of trehalose and external concentration of stabilizing agent can be empirically determined in accordance with the Examples provided herein. The drying buffer may optionally also contain anticoagulants including, but not limited to, citrate and high molecular weight, glass-forming hydroxy-polymers such as PVP and HES.

Alternatively, the platelets can be dried directly without concentration and resuspension if the concentration of trehalose in the final loading reaction mixture is about greater than about 1%. Preferably, the trehalose concentration is about 1 to 25% and the SA concentration is about 0.5% to 5%.

The platelets are then dried. Suitable volumes for drying depend on the method of drying used. For instance, during vacuum drying, aliquots of 100 $\mu$L to 500 $\mu$L are preferred. Any method suitable for use in drying biological materials may be used, including, but not limited to, vacuum, air, spray and lyophilization. Preferably, the method used is vacuum drying. In one exemplary vacuum drying protocol, the vacuum is decreased in a stepwise fashion to a final vacuum in the region of 30 mTorr, keeping the sample temperature above 20° C. and below 38° C. After primary drying of 2–12 hours, the shelf temperature is raised by 0.2° C. per minute to 60° C. and a secondary drying is at 60° C. for 3–6 hours. Optionally, the dried platelets can be terminally sterilised, for instance at 90° C. for 12–24 hrs. Terminal sterilisation is described, for instance in study group of the UK Haemophilia Centre, Directions on Surveillance of Virus Transmission by Concentrates (1988) *Lancet* October 8, pp 814–816.

The containers for drying platelets can be any used in the art. Standard sterile transfusion packs or intravenous saline or parenteral nutrition packs are particularly suitable for the drying and storage of QuadroCytes™ as they enable aseptic processing and rehydration. The transfusion packs also allow direct infusion of the reconstituted QuadroCytes™ without the need for transfer to another container, thus minimizing the risk of contamination. Transfusion bags are particularly suitable as they allow sterile reconstitution through the inlet port. The invention thus encompasses such packs containing QuadroCytes™.

The dried platelets can be stored at ambient temperatures for extended periods of time. Dried platelets are storage stable for at least six weeks at 37° C. in the bags and up to 8 months in glass vials. "Ambient" temperatures or conditions are those at any given time in a given environment. Typically, ambient room temperature is 22° C., ambient atmospheric pressure and ambient humidity are readily measured and will vary depending on the time of year, weather conditions, altitude, etc.

The dried platelets can be reconstituted by resuspension in a physiologically acceptable buffer. For therapeutic use, the buffer is sterile. The buffer can be any buffer of suitable pH. Preferably, the buffer contains a substance or substances that exhibit high colloidal osmotic pressure, including, but not limited to, polyethylene glycol (PEG) and hydroxy-ethyl starch (HES). Preferably, the buffer is 1–5% human serum albumin (HSA) in saline.

The invention further encompasses compositions comprising the platelets obtained by the methods described herein. The compositions include, but are not limited to, dried platelets; and reconstituted dried platelets.

The compositions may further comprise any pharmaceutically acceptable vehicle or excipient. For instance, the dried platelets are particularly suitable for the delivery of therapeutic agents to the reticulo-endothelial system and to sites of haemostatic activity. The dried platelets are also suitable for incorporation into topical ointments, creams such as shaving creams, gels and salves. Pharmaceutical grade organic carriers and/or diluents suitable for topical use are well known in the art. The dried platelets are particularly suitable for inclusion into topical applications for wound healing especially as a delivery vehicle for bioactives with non-scarring and debriding activities. Compositions comprising the reconstituted platelets and vehicles including, but not limited to, powders, ointments, creams and gels are further encompassed by the invention. For use in wound healing, the dried platelets can be incorporated into bandages by incorporation into polymers including synthetic polymers or natural polymers such as collagen.

The reconstituted platelets are particularly suitable for use in transfusions for platelet replacement therapy. Thus, a particularly preferred composition is a suspension of reconstituted dried platelets in a buffer suitable for use in intravenous transfusions. The choices of platelet concentration, and vehicle are well within the skill of one in the art and vary depending on the indication being treated.

As shown herein, the reconstituted platelets retain the characteristics of fresh platelets with respect to in vivo platelet turnover, effect on bleeding time, and effect on the amount of blood loss. In addition, in vitro comparison of the reconstituted platelets and fresh platelets showed good correlation of a number of attributes. These are summarized in Table 1.

TABLE 1

QuadroCytes ™ in vitro

| | |
|---|---|
| GP1b presence | ++ |
| Membrane Sialic Acid | ++ |
| Recovery of platelet Nos. after drying/rehydration | 70–80%* |
| Adhesion to collagen | ++ |
| Procoagulant (PF3) activity | +++ |
| Aggregation | + |
| Aggregation with small number normal platelets | ++ |
| Clot retraction with small number normal platelets | ++ |

*Not recovered platelets had turned into small–large fragments and microparticles. In all in vitro and in vivo experiments, these have been removed by centrifugation.

The invention further encompasses methods for delivering platelets either alone or as delivery vehicles for therapeutic agents. Therapeutic agents are delivered by first preparing platelets loaded with at least one therapeutic agent, as obtained according to the methods described herein. The bioactive agents are loaded into the platelets by any method known in the art during or contemporaneously with loading of the platelets with trehalose. For instance, loading of platelets by electropermeabilisation has been described by Hughes and Crawford (1990). The platelets are then administered to an individual. The platelets can be either administered freshly loaded with the compound, or dried and incorporated into a physiologically acceptable vehicle or reconstituted in solution before administration. The dried platelets are particularly suitable for the delivery of therapeutic agents to the reticulo-endothelial system and to sites of haemostatic activity. The dried platelets are particularly suitable as delivery vehicles for bioactives such as those with non-scarring and debriding activities in wound healing applications.

Therapeutic agents are substances that affect prophylaxis. These are well known in the art and include a wide variety of drugs. The platelets can also be loaded with bioactive compounds. Examples of suitable bioactive compounds include, but are not limited to, stabilizing agents, tracers, fluorescent tags and other imaging substances such as radiolabels, cryoprotectants, nucleic acids, and bioactive materials. Bioactive materials particularly suited to incorporation into platelets include, but are not limited to, haemostatic effectors, wound healing factors, cytokines and drugs. Suitable bioactive materials also include therapeutic and prophylactic agents. Examples of bioactive materials include, but are not limited to, proteins and peptides (synthetic, natural and mimetics), oligonucleotides, viral vectors, hemotherapeutic agents, anti-cancer drugs, antiinflammatory drugs, thrombomodulating agents, immunomodulating agents and the like.

The invention also provides methods for producing platelets suitable for purification of platelet factors. Platelets are prepared as described above and platelet factors may then be isolated from the platelets produced thereby. Examples of platelet factors include, but are not limited to, PDGF, tumor-necrosis factor, thromboglobulin and thrombospondin. The platelet factors can be isolated by any protein purification techniques known in the art. Suitable methods of protein purification known in the art include, but are not limited to, affinity chromatography, immunoaffinity chromatography, size exclusion chromatography, HPLC and FPLC. Any purification scheme that does not result in substantial degradation of the protein is suitable for use in the present invention.

The following examples are meant to illustrate but not limit the invention.

EXAMPLES

Example 1

Loading of Platelets with Trehalose

Platelets were isolated from standard 1–3 day old platelet concentrates prepared from blood collected into CPDA (16 mM Sodium citrate, 29 mM D-glucose, 3.1 mM citric acid, 2.9 mM sodium phosphate 0.36 mM adenine). Following addition of 0.8 $\mu$M prostaglandin $I_2$ and 0.2 $\mu$/mL apyrase (or adjustment to pH 6.5 with citric acid), the platelets were harvested by centrifugation in a Damon/1EC Centra 4R centrifuge at 1200×g for 15 minutes. The supernatant was carefully removed using a plastic Pasteur pipette, making sure to remove all of the supernatant without disturbing the platelet pellet.

For introduction of the trehalose, the platelets are resuspended to a concentration of $1-10\times10^{12}$ cells per mL in a high potassium (75–130 mM), low sodium (1–20 mM) loading buffer containing 30–60 mM trehalose, 7 mM magnesium chloride, 5 mM glucose, 5 mM ATP and electroporated in a Biorad Gene Pulser at 5–7 kV/cm and 3.0 mF (2–5 pulses at 10–30 sec intervals). Following electroporation, the platelets are allowed to reseal for 30–60 min at 37° C. before centrifugation and resuspension in drying buffer.

Trehalose loading was assessed by using radiolabeled sugar or by estimation of the trehalose content of the loaded platelets by hplc analysis. Results of these experiments shown in Table 2 demonstrated that the above treatment permeabilized the membranes and loaded the platelets with trehalose. The morphology (platelet distribution profile and mean platelet volume) of platelets were analyzed by Coulter® Microdiff 18 hematology analyzer. The morphology of platelets before (MPV 6.4–7.7, PDW 15.7–17.2) and after trehalose loading by electroporation (MPV 7.0–7.3, PDW 16.3–18.3) was unchanged and the ATP release response, and platelet aggregation responses to the agonists collagen, thrombin or U 46619, of the trehalose loaded platelets was also within normal levels.

TABLE 2

Trehalose loading of platelets

| Trehalose conc. in loading buffer | $^{14}$C | Hplc |
|---|---|---|
| 30 mM | 21 mM | 21 mM |
| 60 mM | 41 mM | 45 mM |

Example 2

Drying of Platelets Loaded with Trehalose

Platelets were loaded with trehalose as in Example 1 and the resealed platelets adjusted to pH 6.5 with citric acid and centrifuged at room temperature at 1100×g for 7 minutes to pellet the platelets. Supernatant was carefully removed using a plastic Pasteur pipette and the platelet pellets were resuspended in a pH 7.4 drying buffer, containing 100–130 mM sodium chloride, 5 mM potassium chloride, 1 mM magnesium chloride, 5 mM ATP, 1–5% (w/v) serum albumin and 30–100 mM trehalose, to a final platelet count of $1-2 \times 10^{12}$ per liter. For drying in glass pharmaceutical vials the platelets were adjusted to a concentration of $1-2 \times 10^{12}$ per liter and 300 μl of resuspended platelets was carefully pipetted into 3 mL glass vials and vacuum dried in a modified FTS Systems freeze drier. For drying in bags, the platelets were adjusted to a concentration of $2-4 \times 10^{12}$ per liter and 20–25 mL aliquots were injected into standard transfusion bags and vacuum dried in a modified FTS Systems freeze drier.

Vacuum drying was done by programming the following initial settings into the FTS: shelf temperature, 37° C.; vacuum, 30 Torr. Before starting the run the sample temperature was equilibrated to approximately 35° C. During the run the pressure was gradually decreased so that the sample temperature did not fall below 20° C. The following protocol is adjusted for drying twelve, 3 mL vials containing 300 μl of product:

| vacuum (mTorr) | time (min) | shelf temperature (° C.) | approximate product temperature (° C.) |
|---|---|---|---|
| 30,000 | 4 | 37 | 29 |
| 25,000 | 5 | 60 | 27 |
| 20,000 | 3 | 60 | 24 |
| 15,000 | 11 | 60 | 20 |
| 10,000 | 3 | 60 | 24 (product dry) |
| 2,000 | 2 | 20 | 41 |
| 300 | 8 | 20 | 44 |
| 30 | overnight | 30 | 39 |

For reconstitution, the vials were rehydrated by the addition of 600 μl 1–5% SA in a buffered sodium chloride (75 mM) solution (BioProducts Laboratories) and gently mixed, yielding an isotonic suspension of rehydrated platelets. Rehydrated platelets were analyzed by Coulter® Microdiff 18 hematology analyzer and light microscopy. Platelet function was assayed by studying aggregation in response to the following agonists:

| thrombin | 1.0 U/mL (final concentration) |
| collagen | 10 μg/mL (final concentration) |
| ristocetin | 1.5 mg/mL (final concentration) |
| ADP | 10.6 μM (final concentration) |
| U 46619 | 0.2 μM (final concentration) |

Total numbers and morphology of platelets was not altered after drying and rehydration as assayed using light microscopy and the Coulter® Microdiff 18 hematology analyzer and showed no change in morphology after 7 days of storage. Platelets maintained normal morphology as assessed by mean platelet volume (MPV 7.4–8.7) and platelet distribution profile (PDW 17.8–19.3) even after ambient storage for 28 days. The reconstituted platelets exhibited aggregative haemostatic function when treated with agonists listed above.

Example 3

Terminal Sterilisation of Dried Platelets

QuadroCytes™ were loaded with 30–90 mM trehalose by electroporation and dried in glass vials as described in Examples 1 and 2. The sealed glass vials were heated at 80° C. for 24, 48 and 72 hrs. The terminally sterilised samples were reconstituted and tested for aggregative haemostatic function with a variety of agonists as described in Example 2. The reconstituted QuadroCytes™ displayed normal morphology as assessed by light microscopy and showed a normal cell size distribution on a Coulter® Microdiff 18 hematology analyzer even after 72 hrs at 80° C. (MPV 7–7.3 and PDW 16.3–18.3 before, and MPV 7.4–8.7 and PDW 17.8–18.3 after terminal sterilisation). The reconstituted QuadroCytes™ exhibited aggregative haemostatic function when treated with agonists and no significant differences were observed between terminally sterilised platelets at the three time points studied.

Example 4

Analysis of the Surface Properties of Rehydrated QuadroCytes™

QuadroCytes™ dried in both vials and bags were prepared as described in Example 2. Total and neuraminidase-labile sialic acid was estimated by the modification of the thiobarbituric assay as described by Crook and Crawford. (1988) Br. J. Haematol. 69:265. The results obtained are shown in Table 3.

TABLE 3

Total and neuraminidase labile sialic acid of QuadroCytes ™

| | Blood-bank platelets | Vials | Bags |
|---|---|---|---|
| (nmol/10$^9$ platelets) | (n = 7) | (n = 12) | (n = 20) |
| Total content | 40 | 49 | 30 |
| Neuraminidase labile | 24 | 31 | 24 |

Example 5

Functional Analysis of the Cytoplasmic Integrity of Rehydrated QuadroCytes™

QuadroCytes™ dried in both vials and bags were prepared as described in Example 2. Collagen-induced aggregation was assessed by microscopy; rehydrated QuadroCytes™ ($2\times10^{11}$ platelets/L) were stirred with fluorophore PKH26 (Sigma Chemical Co) labelled fresh platelets ($0.5\times10^{11}$ platelets/L) in the presence of 10 µg/mL collagen. The distribution of labelled fresh platelets was random and a greater portion of aggregates was made up of unlabelled rehydrated QuadroCytes™.

Preservation of functional cyclooxygenase and thromboxane $A_2$ synthase activities were assessed by measuring thromboxane $B_2$ generation by rehydrated QuadroCytes™ ($2.5\times10^{11}$ platelets/L) incubated with 50 µM arachidonic acid. Thromboxane $B_2$ generation was measured by a commercial ELISA kit (Cayman Chemical Co.). The generation of thromboxane $B_2$ from its active precursor thromboxane $A_2$ demonstrates the preservation of functional cyclooxygenase and thromboxane $A_2$ synthase activities in dried QuadroCytes™.

Example 6

Indium Labeling of Rehydrated QuadroCytes™ for in vivo Studies

QuadroCytes™ dried in both vials and bags were prepared as described in Example 2. Rehydrated QuadroCytes™ ($5\times10^{11}$ platelets/L) or washed fresh platelets were resuspended in isotonic saline containing 1% serum albumin and $^{111}$Indium oxide (0.925 MBq/$10^9$ platelets) for 30 min at room temperature. The labeling efficiency of the rehydrated QuadroCytes™ was comparable to that of the fresh washed platelets (both ~10%) and no loss of radioactive label was observed when the radiolabelled platelets were incubated in plasma over a 2 hr period confirming the cytoplasmic integrity of the dried, rehydrated QuadroCytes™.

Example 7

In vivo Testing of the Reconstituted Platelets

Figure 2:
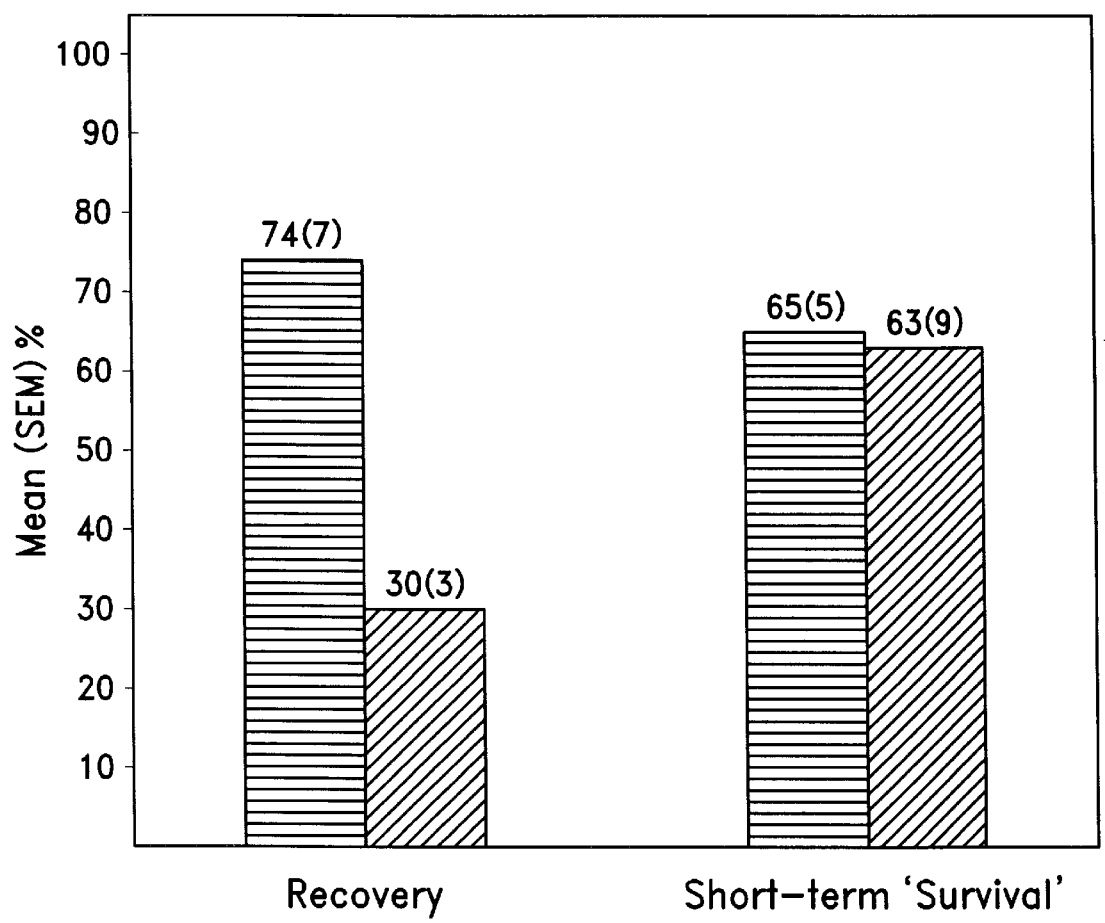
FIG. 2 is a bar graph depicting the percentage recovery and short-term platelet "survival" after intravenous injection of platelets (horizontal-hatch bar) or rehydrated QuadroCytes™ (oblique-hatch bar). Recovery is defined as the percentage of the total injected platelets that can be recovered from the blood after 1 hour. Short-term survival is defined as the percentage of the injected platelets present in the blood 1 hour after administration that are still present after another 3 hours of circulation.
Figure 3:
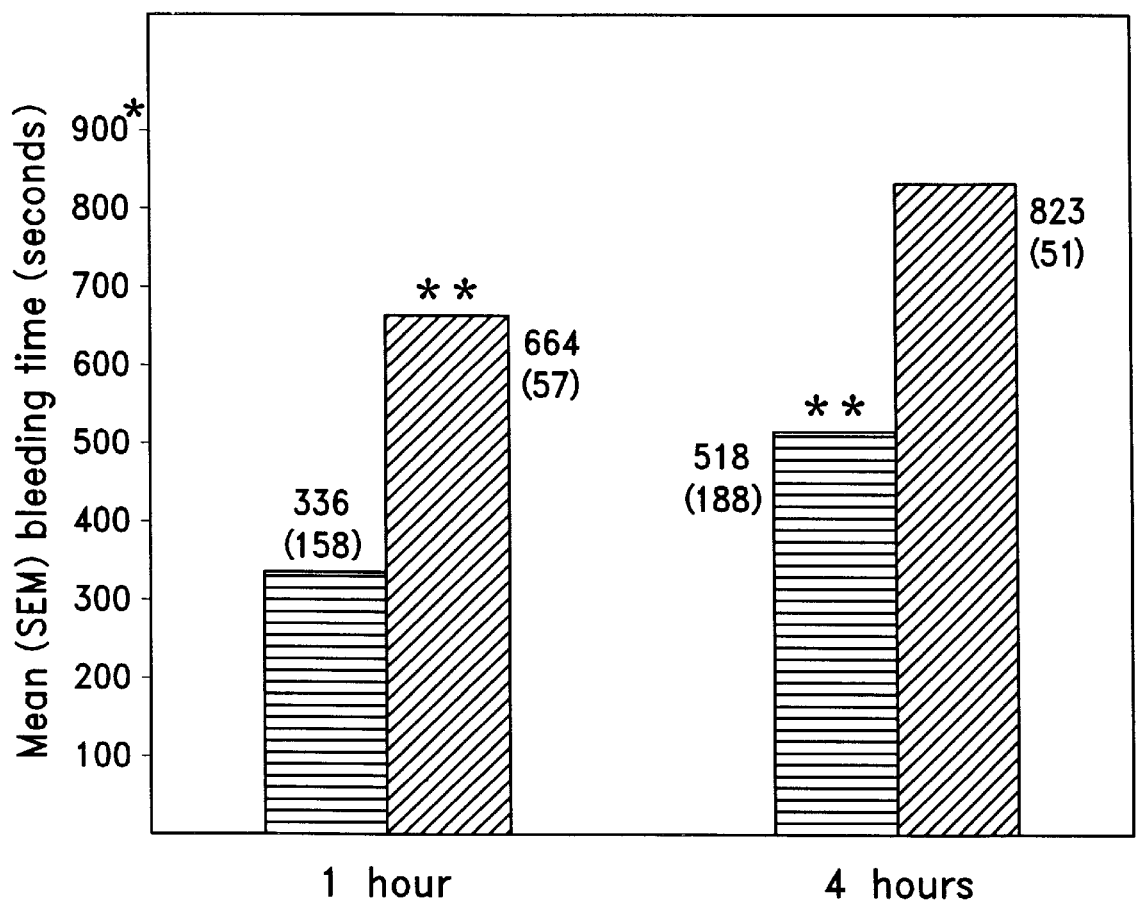
FIG. 3 is a bar graph depicting the bleeding time measured after earcut-induced bleeding performed 1 and 4 hours after intravenous bolus injection of platelets (horizontal-hatch bar) or rehydrated QuadroCytes™ (oblique-hatch bar).
Figure 4:
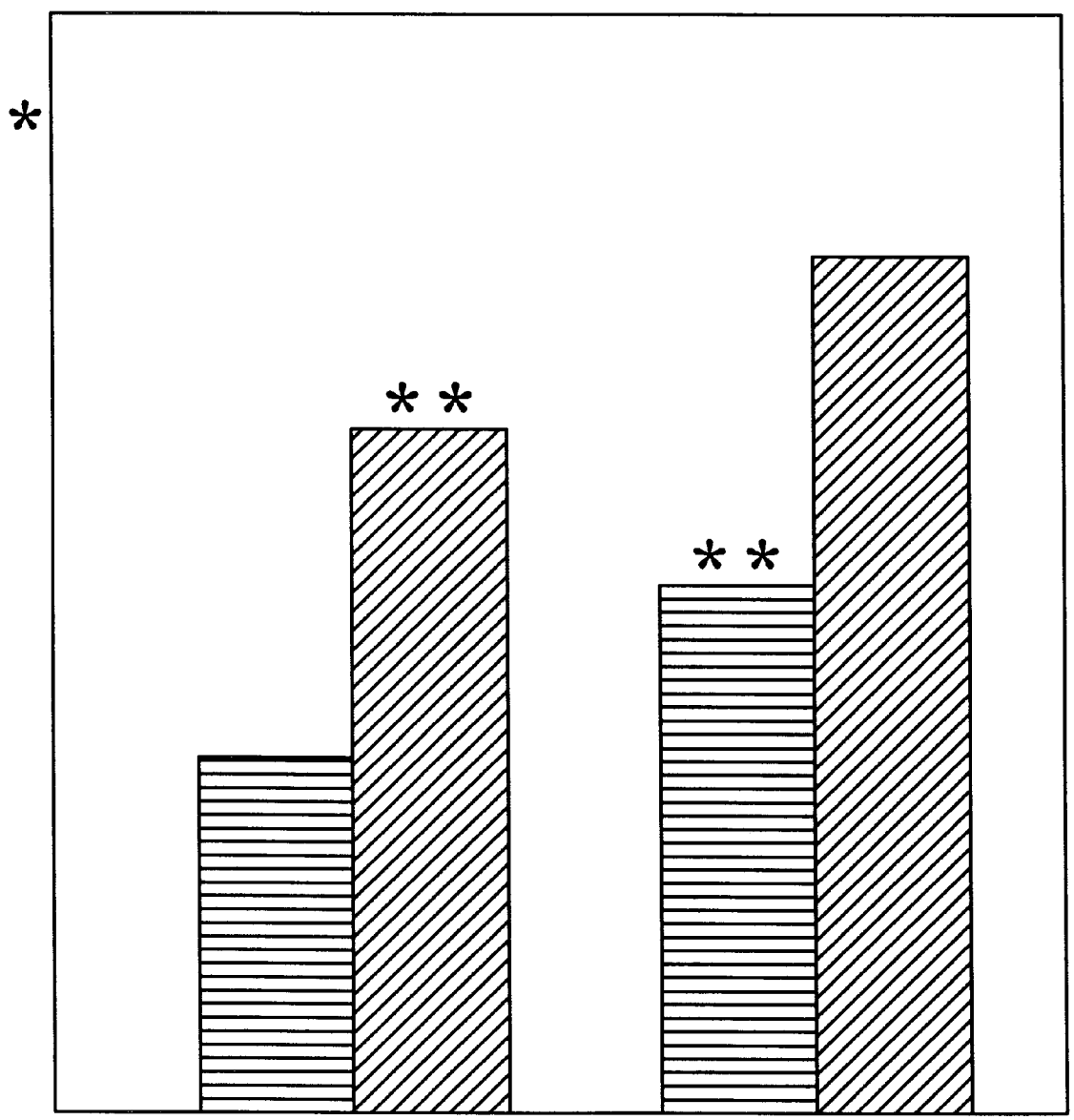
FIG. 4 is a bar graph depicting bleeding time in rabbits treated with platelets (horizontal-hatch bar) or rehydrated QuadroCytes™ (oblique-hatch bar). The asterisks represent the times at which the numbers of platelets and rehydrated QuadroCytes™ were comparable in the blood.
Figure 5:
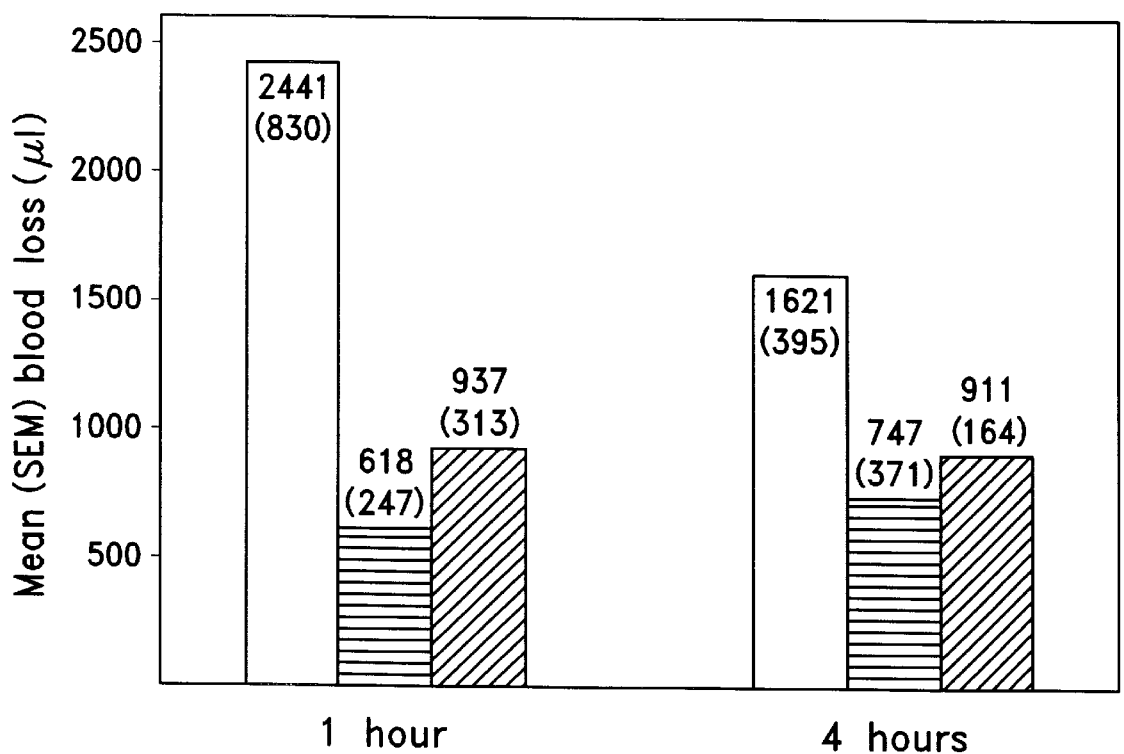
FIG. 5 is a bar graph depicting the amount of blood lost from earcut 1 and 4 hours after intravenous bolus injection of vehicle (white bar); platelets (horizontal-hatch bar) or rehydrated QuadroCytes™ (oblique-hatch bar).

QuadroCytes™ dried in vials were prepared as described in Example 2 and stored at ambient temperatures for 2–6 weeks before transportation, under normal non-refrigerated air cargo conditions from Cambridge, England to Ontario, Canada where they were assayed for survival and haemostatic function in vivo. Function of the reconstituted QuadroCytes™ was assessed using the RES-block thrombocytopenic rabbit model developed by Blajchman. Ali et al. (1994). The recovery and survival of reconstituted QuadroCytes™ after intravenous bolus injection of $2-4\times10^{10}$ platelets is shown in FIGS. 1 and 2 respectively, showing a recovery of ~30% after 1 hour and short-term survival of ~63% after 3 hours circulation. The effects of reconstituted QuadroCytes™ on bleeding times and blood loss is shown in FIGS. 3 and 4 respectively, showing significant haemostatic activity of the reconstituted platelets.

QuadroCytes™ dried to a water content of <6% showed no loss of in vivo functional activity after stored at temperatures ranging from 4–30° C. for 3–4 months as assessed by effect on blood loss in the Blajchman RES-block thrombocytopenic rabbit model.

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

What is claimed is:

1. A method for preserving platelets in a form stable at ambient temperature or above, the method comprising:
   a) treating a suspension of isolated platelets under conditions effective to introduce into the platelets 5–150 mM of internal trehalose; and
   b) drying the platelets in the presence of an amount of external carbohydrate effective to preserve the platelets on drying.

2. The method according to claim 1, wherein the external carbohydrate is trehalose.

3. The method according to claim 1, wherein the internal trehalose concentration is 10–39 mM.

4. The method according to claim 1, wherein the internal trehalose concentration is 20–60 mM.

5. The method according to claim 2, wherein the external trehalose concentration is 1–30%.

6. The method according to claim 2, wherein the external trehalose is in a drying buffer.

7. The method according to claim 6, wherein the drying buffer further comprises serum albumin.

8. A composition comprising dried platelets comprising 5–150 mM of internal trehalose and external carbohydrate.

9. A storage-stable pack comprising the composition of claim 8.

10. The method of claim 1, wherein step b) comprises vacuum drying the platelets.

11. The method of claim 1, wherein step a) comprises electropermeabilisation of the platelets.

* * * * *